United States Patent [19]

van Zelderen

[11] Patent Number: Plant 7,411

[45] Date of Patent: Jan. 1, 1991

[54] ALSTROEMERIA NAMED ZELROSA

[76] Inventor: Gerard J. van Zelderen, Achterweg 34-36, 1424 PR De Kwakel, Netherlands

[21] Appl. No.: 367,232

[22] Filed: Jun. 14, 1989

[51] Int. Cl.[5] ..... A01H 5/00
[52] U.S. Cl. ..... Plt./68
[58] Field of Search ..... Plt./68

*Primary Examiner*—James R. Feyrer
*Attorney, Agent, or Firm*—Charles W. Rummler

[57] ABSTRACT

A new and distinct variety of Alstroemeria plant particularly distinguished by its continuous and profuse production of very large flowers having a rose bengal coloration, in general, highlighted by the white central portion of the inner petals of each of the flowers comprising the bloom, the umbel cluster of each bloom having three to seven flowers of relatively large size each carried on a strong upright stem of a length between 6 and 9 cm. depending upon season. The height of the plant varies with the season, between 60 and 150 cm., with each blooming cane varying in length between those heights thereby simplifying harvesting for cut flowers.

1 Drawing Sheet

BACKGROUND OF THE NEW PLANT

My new Alstroemeria cultivar originating as a seedling of a hybrid developed by me by crossing unknown varieties selected from miscellaneous plants comprising my collection of Alstroemeria maintained by me at my greenhouse in DeKwakel, Holland and the present plant was selected by me from the several seedlings of the said hybrid because of the very large size of its flowers and a coloration which I consider to have good commercial merit. This selected seedling was propagated by me from roots and such propagation was carried on through several successive generations at DeKwakel which demonstrated that the novel characteristics of this variety would hold true from generation to generation and its homogeneity could thereby be assured for propagation on a commercial scale. Commercial propagation of this new variety is done under my direction at DeKwakel, Holland and the new plant is also being grown in greenhouse at Aalsmeer, whereby its character can be independently judged.

DESCRIPTION OF THE DRAWING

This new Alstroemeria cultivar is illustrated by the accompanying photographic drawing which shows face views of a number of the flowers comprising an umbel cluster, the color rendition being as nearly true to those specified herein as is possible to obtain by conventional photographic procedures.

DESCRIPTION OF THE NEW PLANT

The following is a detailed description of my new Alstroemeria cultivar as observed in September 1988 from flowers grown in greenhouse at Aalsmeer, Holland the color designations being acording to The R.H.S. Colour Chart of the Royal Horticultural Society of London, England.

THE PLANT

Origin: Seedling.
Parentage: Unknown.
Classification: Alstroemeria Hybrid.
Form: A tall, erect bush.
Height: Varying with the season between 60 and 150 cm. with each blooming cane varying in length between those heights.

Branching: This plant does not branch.
Growth Habit: This plant is fast growing with vigorous, upright stems of good strength.
Foliage:
- *Quantity.*—Moderate.
- *Leaf size.*—12 to 18 cm. long and about 2 to 4 cm. in width.
- *Leaf shape.*—Elliptical with entire margins.
- *Texture.*—Leathery.
- *Color.*—Upper side — glossy green. Under side — medium green.

Rizomes:
- *Color.*—White.
- *Size.*—Depending upon season.

THE BUD

Size: Medium.
- *Diameter.*—About 1.5 cm.
- *Length.*—About 3 cm.

Form: Pear-shaped.
Opening rate: Normal.
Sepals:
- *Number.*—Six.
- *Shape.*—Elliptical.
- *Color of petals.*—When sepals divide and when petals begin to unfurl Neyron Rose, R.H.S. 55-B.

Flower Stem:
- *Length.*—Between 6 and 9 cm. depending on season and growing conditions.
- *Character.*—Strong and erect.
- *Color.*—Middle green.

THE INFLORESCENCE

Blooming Habit: Continuous the year around.
Size of flower: Very large.
- *Diameter.*—About 7 cm.
- *Dept.*—About 6 cm.

Borne: Singly on a stem of an umbel cluster of 3 to 7 flowers. Averaging about 5.
Shape: Funnel-shaped with petal tips curling outwardly.
Petalage:
- *Number of petals.*—Six.
- *Arrangement.*—Two concentric circles of three petals each.
- *Texture.*—Leathery.

*Appearance.*—Shiny.

*Color.*—Outer petals, Body — Neyron Rose 55-B with a base portion of 55-C. Reverse side — White, 155-B. Inside petals — the end portion and the base of each petal — Neyron Rose, 55-C.

The main body portion of the parallel upper petals being White, 155-B. All of the petals, both inner and outer are covered end to end with short, dark pencil stripes extending longitudinally of the petals.

Flower Stem:

*Length.*—About 4 to 5 cm.

*Color.*—Green.

Discoloration after full bloom: The petal coloration tends to run toward pink-red.

Persistence: The flower petals stay on the stem for more than two weeks after becoming fully open.

Lasting quality: On the plant, about 4 weeks, as a cut flower, about 3 weeks.

THE REPRODUCTIVE ORGANS

Stamens:

*Number.*—Six.

*Arrangement.*—One opposite each petal.

*Anthers.*—Size: About 6 mm. Color: Grey.

*Filaments.*—Length: About 4 cm. Color: R.H.S. 55-B.

*Pollen.*—Color: Grey.

Pistils:

*Number.*—One.

*Style.*—Length: About 4 cm.

Color: R.H.S. 55-B.

*Stigma.*—Color: R.H.S. 55-B.

THE FRUIT

Fertility: The fruit is fertile.

Shape: Capsular.

Color: At maturity light brown.

I claim:

1. The new and distinctive Alstroemeria cultivar, substantially as herein shown and described, characterized by the generally Neyron Rose coloration of its very large blooms and distinguished in particular by the white coloration of a major body portion of the upper substantially parallel inside petals of the flowers.

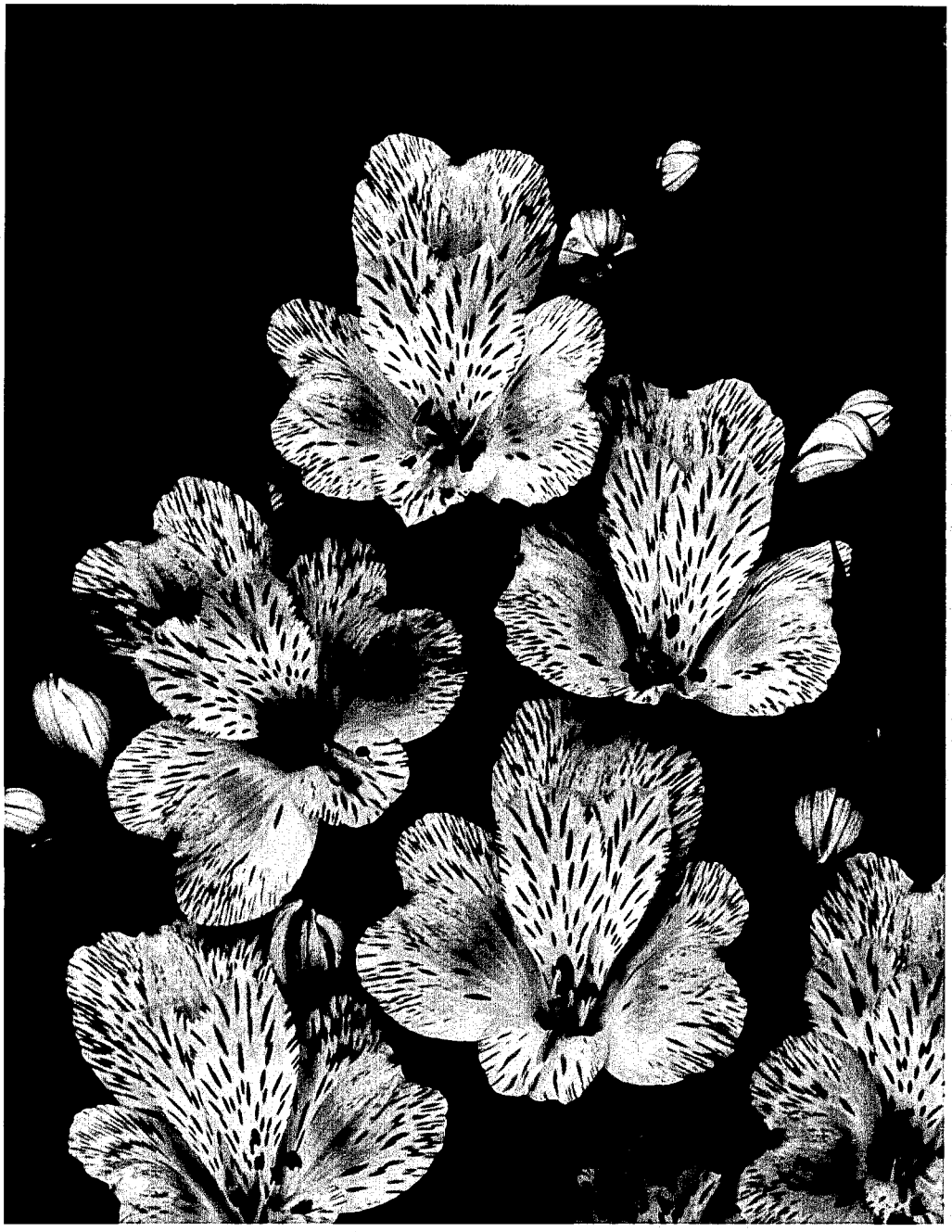

* * * * *